United States Patent
Teshigahara et al.

(10) Patent No.: US 9,739,675 B2
(45) Date of Patent: Aug. 22, 2017

(54) SURFACE ACOUSTIC WAVE SENSOR

(71) Applicants: DENSO CORPORATION, Kariya, Aichi-pref. (JP); TOHOKU UNIVERSITY, Aoba-ku, Sendai-shi, Miyagi (JP); National University Corporation Chiba University, Inage-ku, Chiba-shi, Chiba (JP)

(72) Inventors: Akihiko Teshigahara, Nisshin (JP); Toshihiko Takahata, Tokai (JP); Takao Iwaki, Miyoshi (JP); Shuji Tanaka, Sendai (JP); Masayoshi Esashi, Sendai (JP); Kenya Hashimoto, Chiba (JP)

(73) Assignees: DENSO CORPORATION, Kariya (JP); TOHOKU UNIVERSITY, Sendai-shi (JP); National University Corporation Chiba University, Chiba-shi (JP)

( * ) Notice: Subject to any disclaimer, the term of this patent is extended or adjusted under 35 U.S.C. 154(b) by 204 days.

(21) Appl. No.: 14/722,645

(22) Filed: May 27, 2015

(65) Prior Publication Data

US 2015/0357551 A1  Dec. 10, 2015

(30) Foreign Application Priority Data

Jun. 5, 2014 (JP) ................... 2014-116610

(51) Int. Cl.
*H01L 41/047* (2006.01)
*G01N 29/04* (2006.01)
(Continued)

(52) U.S. Cl.
CPC .......... *G01L 9/0025* (2013.01); *G01L 9/0041* (2013.01); *G01N 29/2462* (2013.01);
(Continued)

(58) Field of Classification Search
CPC ..... G01N 29/2462; G01N 2291/02827; G01N 2291/0423; G01N 2291/02872; G01L 9/0025; G01L 9/0041
(Continued)

(56) References Cited

U.S. PATENT DOCUMENTS

| | | | | |
|---|---|---|---|---|
| 7,758,979 | B2 * | 7/2010 | Akiyama | B81B 3/0021 428/698 |
| 2006/0032312 | A1 * | 2/2006 | Auner | B82Y 10/00 73/570 |

(Continued)

FOREIGN PATENT DOCUMENTS

| | | | |
|---|---|---|---|
| JP | 60169210 | * | 2/1985 |
| JP | 2010088141 | * | 4/2010 |
| WO | WO2008908949 | * | 9/1989 |

OTHER PUBLICATIONS

Akihiko Teshigahara, Ken-ya Hashimoto, Morito Akiyama, "Scandium Aluminum Nitride: Highly Piezoeletric Thin Film for RF SAW Devices in multi GHz Range", 2012 IEEE International Ultrasonics Symposium (IUS).
(Continued)

*Primary Examiner* — J M Saint Surin
(74) *Attorney, Agent, or Firm* — Posz Law Group, PLC

(57) ABSTRACT

A surface acoustic wave (SAW) sensor includes a surface acoustic wave material and a comb-teeth electrode. The surface acoustic wave material is to be arranged at a place where the surface acoustic wave material is distorted by physical quantity such as stress. The comb-teeth electrode is arranged on the surface of the surface acoustic wave material to excite a surface acoustic wave to the surface acoustic wave material. The surface acoustic wave material has a sapphire board and a ScAlN film arranged on a surface of the sapphire board.

11 Claims, 6 Drawing Sheets

(51) Int. Cl.
*G01L 9/00* (2006.01)
*G01N 29/24* (2006.01)

(52) U.S. Cl.
CPC .............. *G01N 2291/02827* (2013.01); *G01N 2291/02872* (2013.01); *G01N 2291/0423* (2013.01)

(58) Field of Classification Search
USPC .......................................................... 73/584
See application file for complete search history.

(56) References Cited

U.S. PATENT DOCUMENTS

| | | | | |
|---|---|---|---|---|
| 2007/0182279 | A1* | 8/2007 | Kawano ................ | G06F 3/0433 310/313 R |
| 2010/0088141 | A1* | 4/2010 | Hill ........................ | G06Q 10/06 705/7.25 |
| 2010/0186514 | A1 | 7/2010 | Teshigahara et al. | |
| 2011/0156828 | A1* | 6/2011 | Kawano ............. | H03H 9/02574 331/116 R |
| 2011/0156840 | A1* | 6/2011 | Kawano ............. | H03H 9/02574 333/193 |
| 2015/0303895 | A1* | 10/2015 | Ballandras ............ | H01L 41/047 310/313 R |

OTHER PUBLICATIONS

Fujii et al., "Wideband Surface Acoustic Wave Device in a Few GHz Range Using ScAlN/Single Crystal Diamond Structure", vol. J96-A No. 6 pp. 351-356, Jun. 1, 2013, IEICE Transactions on Fundamentals of Electronics, Communications and Computer Sciences (Japanese Edition).

* cited by examiner

SURFACE ACOUSTIC WAVE SENSOR

CROSS REFERENCE TO RELATED APPLICATION

This application is based on Japanese Patent Application No. 2014-116610 filed on Jun. 5, 2014, the disclosure of which is incorporated herein by reference in its entirety.

TECHNICAL FIELD

The present disclosure relates to a surface acoustic wave (SAW) sensor.

BACKGROUND

A surface acoustic wave (SAW) sensor detects physical quantity such as pressure, load or acceleration by converting the physical quantity to a distortion of a SAW device. Specifically, the physical quantity is detected by detecting change in frequency, delay time, and phase of the SAW device.

Teshigahara, Akihiko; Hashimoto, Ken-ya; Akiyama, Morito "Scandium Aluminum Nitride: Highly Piezoelectric Thin Film for RF SAW Devices in multi GHz Range", 2012 IEEE INTERNATIONAL ULTRASONICS SYMPOSIUM (IUS) describes a SAW device using SAW material having ScAlN/SiC structure. The SAW material has ScAlN film on the surface of SiC board. The ScAlN film is a piezoelectric thin film, and the SiC board is a non-piezoelectric board.

Since the piezoelectricity of ScAlN film is high, the SAW characteristic of SAW device having the ScAlN/SiC structure is excellent. Further, the SAW device can be used under high temperature environment since the heat resistance of ScAlN film is high. The SAW device having the ScAlN/SiC structure may be used in the surface acoustic wave sensor to realize a sensor with high sensitivity that can be used under high temperature environment.

In this case, however, an amount of change in frequency, delay time, and phase of SAW element is made smaller by the acoustoelastic effect when the SAW material is distorted by physical quantity, such that the detection sensitivity (sensing accuracy) of physical quantity may be lowered. The acoustoelastic effect is phenomenon in which the propagation speed of SAW in the SAW material is changed by stress (distortion).

SUMMARY

It is an object of the present disclosure to provide a surface acoustic wave sensor having higher detection sensitivity of physical quantity compared with a case where a SAW material having a ScAlN/SiC structure is used.

According to an aspect of the present disclosure, a surface acoustic wave sensor includes a surface acoustic wave material and a comb-teeth electrode. The surface acoustic wave material is to be arranged at a place where the surface acoustic wave material is distorted by physical quantity. The comb-teeth electrode is arranged on the surface acoustic wave material to excite surface acoustic wave to the surface acoustic wave material. The surface acoustic wave material has a sapphire board and a ScAlN film arranged on a surface of the sapphire board.

The acoustoelastic effect of the SAW material having the ScAlN/sapphire structure, in which the ScAlN film is formed on the surface of the sapphire board, is very smaller than that of the SAW material having the ScAlN/SiC structure.

Since the SAW material having such ScAlN/sapphire structure is used in the present disclosure, the acoustoelastic effect affecting change in frequency, delay time or phase of the SAW element can be smaller, compared with the case where the SAW material having the ScAlN/SiC structure is used. Therefore, the detection sensitivity of physical quantity can be raised.

A Sezawa wave or a Rayleigh wave may be used as SAW. According to an aspect of the present disclosure, it may be desirable to use a Sezawa wave as SAW.

It is known that the distribution ratio of the SAW energy into the substrate becomes larger in the depth direction as the mode of SAW is made higher-order, in a SAW material having a general structure, in which a piezoelectric thin film is arranged on a substrate. In other words, as the mode of SAW is made higher-order, the SAW energy can be distributed to the deep side deeper from the surface of SAW material. For this reason, compared with a case where Rayleigh wave is used, the sapphire board strongly affects the acoustoelastic effect when using Sezawa wave, such that the acoustoelastic effect can be reduced.

Therefore, the detection sensitivity of physical quantity can be much raised when Sezawa wave is used as SAW.

BRIEF DESCRIPTION OF THE DRAWINGS

The above and other objects, features and advantages of the present disclosure will become more apparent from the following detailed description made with reference to the accompanying drawings. In the drawings.

DETAILED DESCRIPTION

Figure 1:
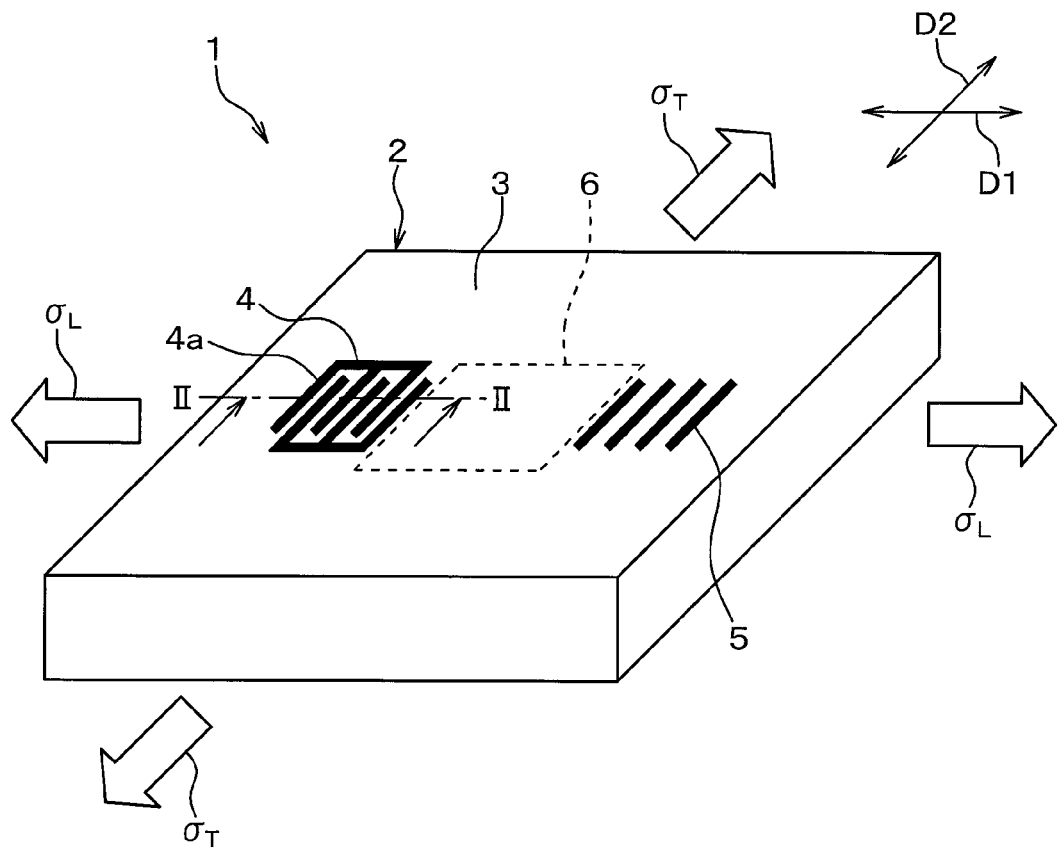
FIG. 1 is a perspective view illustrating a sensor chip of SAW sensor according to a first embodiment.

Embodiments of the present disclosure will be described hereafter referring to drawings. In the embodiments, a part that corresponds to a matter described in a preceding embodiment may be assigned with the same reference numeral, and redundant explanation for the part may be omitted. When only a part of a configuration is described in an embodiment, another preceding embodiment may be applied to the other parts of the configuration. The parts may be combined even if it is not explicitly described that the parts can be combined. The embodiments may be partially combined even if it is not explicitly described that the embodiments can be combined, provided there is no harm in the combination.

First Embodiment

A surface acoustic wave (SAW) sensor 1 detects pressure or load as physical quantity. For example, the SAW sensor 1 is used as a combustion pressure sensor that detects combustion pressure in an internal combustion engine.

As shown in FIG. 1, the SAW sensor 1 has a sensor chip 2. The sensor chip 2 includes a SAW material 3, a comb-teeth electrode (inter digital transducer) 4 and a reflector 5. The comb-teeth electrode 4 and the reflector 5 correspond to electrodes formed on the SAW material 3.

The comb-teeth electrode 4 excites the SAW material 3 to oscillate. The reflector 5 reflects SAW transmitted from the comb-teeth electrode 4. The domain between the comb-teeth electrode 4 and the reflector 5 on the surface of the SAW material 3 corresponds to a propagation path 6 in which SAW is transmitted. The comb-teeth electrode 4, the reflector 5, and the propagation path 6 correspond to a reflective delay type SAW element.

The comb-teeth electrode 4 includes a pair of electrodes having plural comb-teeth parts 4a extending parallel to each other. The reflector 5 includes plural linear electrodes arranged parallel to each other. The linear electrodes of the reflector 5 extend parallel to the comb-teeth part 4a. A high frequency signal (burst signal) corresponding to the resonance frequency of the comb-teeth electrode 4 is applied to the comb-teeth electrode 4 to drive the comb-teeth electrode 4. SAW is excited to the SAW material 3 by driving the comb-teeth electrode 4, and spreads in a perpendicular direction perpendicular to the comb-teeth part 4a of the comb-teeth electrode 4. As shown in FIG. 1, the direction D1 represents the propagation direction of SAW, and the direction D2 represents the perpendicular direction perpendicular to the propagation direction of SAW.

In this specification, SAW means a Rayleigh wave type surface acoustic wave having plural modes. The 0th mode (lowest order) of the Rayleigh wave type surface acoustic wave is a Rayleigh wave. The 1st mode (primary mode) of the Rayleigh wave type surface acoustic wave is a Sezawa wave. In this embodiment, Sezawa wave is used as SAW. The comb-teeth electrode 4 is configured to excite Sezawa wave.

Figure 2:
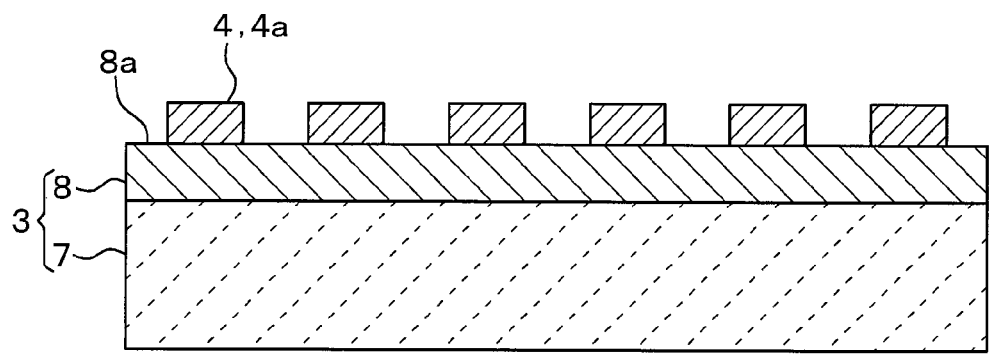
FIG. 2 is a cross-sectional view taken along a line II-II in FIG. 1.

The SAW material 3 has ScAlN/sapphire structure. Specifically, as shown in FIG. 2, the SAW material 3 includes a sapphire board 7 which is a non-piezoelectric board, and a ScAlN (aluminum nitride containing scandium, scandium doped aluminum nitride) film 8 which is a piezoelectric thin film directly formed on the surface of the sapphire board 7.

As the sapphire board 7, for example, the substrate surface has the plane direction (orientation) of C-plane, and the propagation direction of SAW is inside of A-plane or in a direction defined by rotating by 60 degrees relative to the A-plane. Under this condition, the SAW characteristic is better.

The ScAlN film 8 is a film produced by adding Sc to AlN. When the sum of Sc and Al is defined as 100 atom %, it is desirable to set the concentration of Sc to the ScAlN film 8 as 40-50 atom %. In this case, the piezoelectric constant can be made the highest. In this embodiment, the electrodes 4 and 5 are formed on the upper surface 8a of the ScAlN film 8 away (opposite and distanced) from the sapphire board 7, as shown in FIG. 2.

Figure 3:
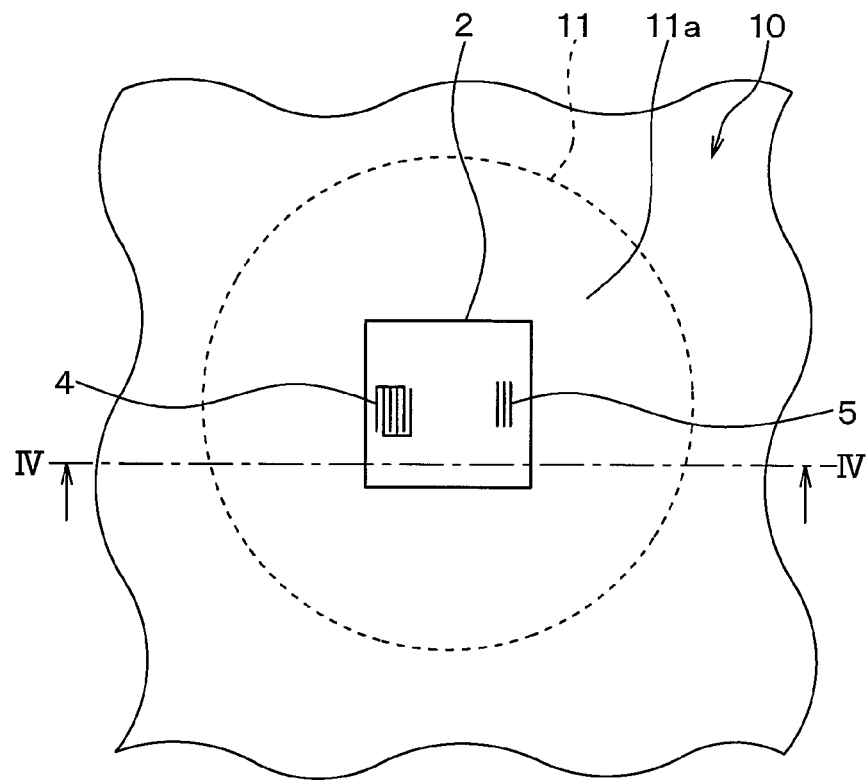
FIG. 3 is a plan view illustrating a diaphragm structure to which the sensor chip is installed.
Figure 4:
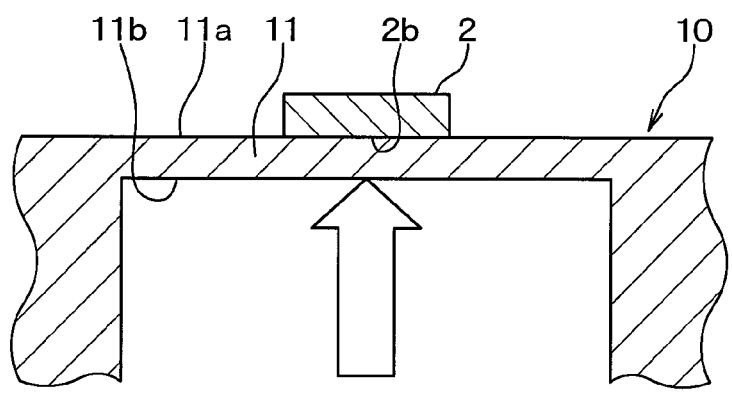
FIG. 4 is a cross-sectional view taken along a line IV-IV in FIG. 3.

As shown in FIGS. 3 and 4, the sensor chip 2 is disposed on the first surface 11a of the diaphragm 11 of the diaphragm structure 10. As shown in FIG. 3, the diaphragm 11 has the circle shape. The diaphragm 11 has the second (back) surface 11b opposite from the first surface 11a. When the second (back) surface 11b receives pressure or load in a direction shown by an arrow in FIG. 4, the diaphragm 11 is distorted and deformed. For this reason, the diaphragm 11 has concentric-circle stress distribution with a center corresponding to the center position of the diaphragm 11. In this embodiment, the diaphragm structure 10 is made of metal. However, the diaphragm structure 10 may be made of other materials. The shape of the diaphragm 11 is not limited to circle and may be other form such as square. In this case, the diaphragm 11 has point-symmetry stress distribution with a reference position corresponding to the center position of the diaphragm 11.

The whole of the back surface 2b of the sensor chip 2 is fixed to the first surface 11a of the diaphragm 11 through an adhesive layer (not shown). For this reason, when pressure or load is applied to the back surface 11b of the diaphragm 11, the sensor chip 2 is distorted and deformed similarly to the diaphragm 11, and tensile stress is applied to the sensor chip 2. The tensile stress has stress component in all the directions on the surface of the sensor chip 2. As shown in FIG. 1, the tensile stress is presented by being divided into a stress $\sigma_L$ in the propagation direction D1 of SAW and a stress $\sigma_T$ in the perpendicular direction D2 perpendicular to the propagation direction of SAW. Thus, the sensor chip 2 is arranged at a position where the stress $\sigma_L$ in the propagation direction D1 and the stress $\sigma_T$ in the perpendicular direction D2 are applied to the sensor chip 2.

The SAW sensor 1 detects pressure or load as follows. When the comb-teeth electrode 4 is driven, SAW is excited to oscillate the surface of the SAW material 3, and the comb-teeth electrode 4 receives SAW reflected by the reflector 5. At this time, when the back surface 11b of the diaphragm 11 receives pressure or load, the diaphragm 11 and the sensor chip 2 are distorted and deformed. That is, the sensor chip 2 is distorted by the pressure or load. Thereby, since the length of the propagation path 6 of the SAW material 3 is changed, the phase of SAW reflected by the reflector 5 and received by the comb-teeth electrode 4 is changed relative to the phase of SAW excited by the comb-teeth electrode 4. The amount of change in the phase is detected, and pressure or load is computed based on the detected amount of change in the phase, since there is a predetermined relationship between the amount of change in the phase and pressure or load. Therefore, in this embodiment, the amount of change in the phase corresponds to a sensor output.

The phase of SAW is detected by a phase detector circuit (not shown). Further, a calculator (not shown) calculates the amount of phase change, and calculates pressure or load based on the amount of phase change.

The SAW sensor 1 of the present embodiment is compared with a SAW sensor of a first comparative example, in which a SAW material having ScAlN/SiC structure is used.

The other configuration of the SAW sensor of the first comparative example is the same as that of the SAW sensor 1 of the first embodiment.

The detection sensitivity of the SAW sensor 1 of this embodiment and the SAW sensor of the first comparative example is higher as the amount of phase change is larger relative to a distortion of a sensor chip distorted by pressure or load, and is expressed with the following Formula 1.

$$s = s_e + \alpha\sigma_L + \beta\sigma_T \quad \text{Formula 1}$$

s: detection sensitivity, corresponding to a value calculated by dividing the amount of phase change (deg) by the load (N)

$s_e$: a value calculated by dividing the amount of phase change caused by the extended length of the propagation path (deg) by the load (N)

$\sigma_L$: a value calculated by dividing the stress in the propagation direction (Pa) by the load (N)

$\sigma_T$: a value calculated by dividing the stress in the perpendicular direction (Pa) by the load (N)

α: first (longitudinal) acoustoelastic coefficient

β: second (transverse) acoustoelastic coefficient

When a tensile stress is generated, $\sigma_L$ and $\sigma_T$ have positive value. Formula 1 is explained in case where physical quantity is a load. In Formula 1, the term of $\alpha\sigma_L$ and the term of $\beta\sigma_T$ correspond to acoustoelastic effect.

In the first embodiment, the SAW sensor 1 with the ScAlN/sapphire structure has the first acoustoelastic coefficient α of 0.065 and the second acoustoelastic coefficient β of −0.04.

In the first comparative example, the SAW sensor with the ScAlN/SiC structure has the first acoustoelastic coefficient α of −0.32 and the second acoustoelastic coefficient β of 0.12.

TABLE 1

|  | SAW material | α | β |
|---|---|---|---|
| first comparative example | ScAlN/SiC | −0.32 | 0.12 |
| first embodiment | ScAlN/sapphire | 0.065 | −0.04 |

The above acoustoelastic coefficients α, β are calculated as follows by inventors of the present disclosure.

Figure 5:
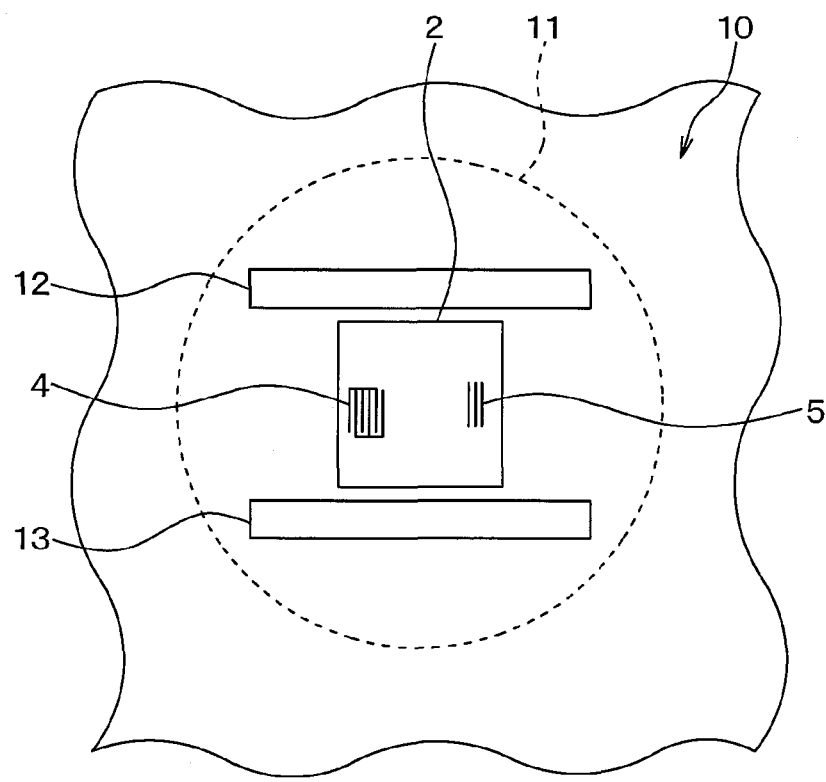
FIG. 5 is a plan view illustrating a diaphragm structure used for experiments to calculate acoustoelastic coefficient of SAW material.
Figure 6:
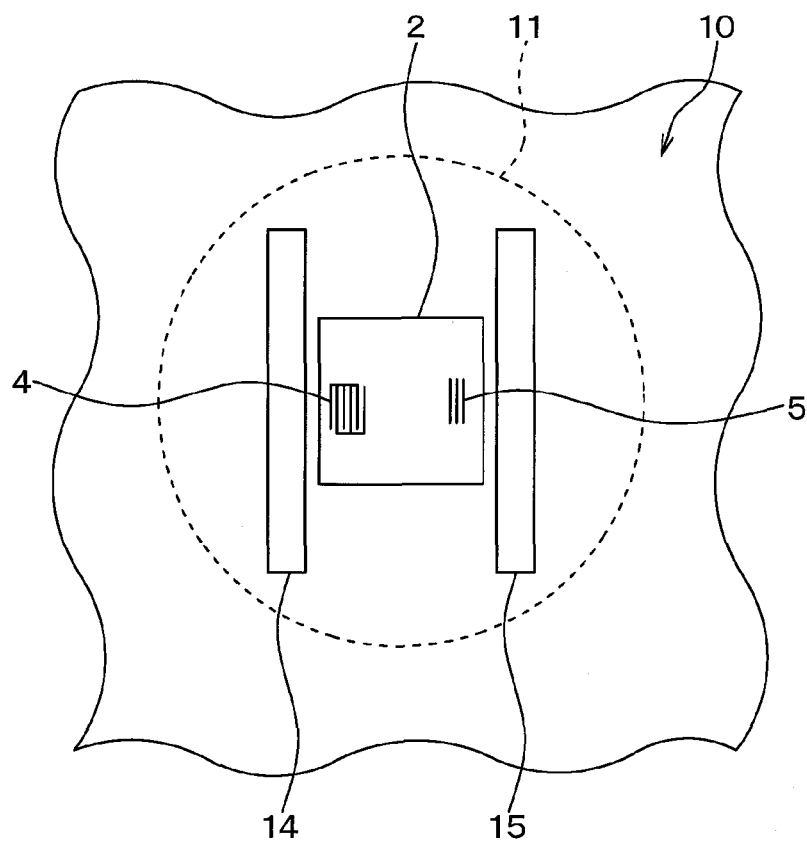
FIG. 6 is a plan view illustrating a diaphragm structure used for experiments to calculate acoustoelastic coefficient of SAW material.

Two of the sensor chips 2 of this embodiment are prepared. One of the sensor chips 2 is arranged on a diaphragm structure 10 made of metal shown in FIG. 5, and the other is arranged on a diaphragm structure 10 made of metal shown in FIG. 6. FIG. 5 is referred to a first sample, and FIG. 6 is referred to a second sample. The conditions such as size/dimension of the sensor chip 2 of the present embodiment are as follows. As to the first comparative example, sensor chips having the same conditions as the first embodiment are prepared.

Thickness of ScAlN film: 2 μm, not affecting the detection sensitivity

Material and thickness of comb-teeth electrode and reflector: Au, 50 nm, not affecting the detection sensitivity Wavelength: 4 μm Length of propagation path: 1.5 mm Comb-teeth electrode number: 40 pairs, not affecting the detection sensitivity Reflector number: 80, not affecting the detection sensitivity Drive frequency in the first comparative example: 1.6 GHz Drive frequency in the first embodiment: 1.45 GHz As shown in FIG. 5, the diaphragm structure 10 has slits (openings) 12 and 13 extending in the propagation direction. The slit 12 is formed along and adjacent to a first side of the sensor chip 2 extending parallel with the propagation direction in the diaphragm 11. The slit 13 is formed along and adjacent to a second side of the sensor chip 2 extending parallel with the propagation direction in the diaphragm 11.

As shown in FIG. 6, the diaphragm structure 10 has slits (openings) 14 and 15 extending in the perpendicular direction. The slit 14 is formed along and adjacent to a third side of the sensor chip 2 extending perpendicularly to the propagation direction in the diaphragm 11. The slit 15 is formed along and adjacent to a fourth side of the sensor chip 2 extending perpendicularly to the propagation direction in the diaphragm 11.

The positional relationship between the slit and the propagation direction on the sensor chip is different between the first sample and the second sample. Therefore, when a load is applied to the diaphragm 11, $\sigma_L$ and $\sigma_T$ in Formula 1 differ between the first sample and the second sample. For this reason, Formula 2 is obtained from the first sample, and Formula 3 is obtained from the second sample.

$$s(1) = s_e(1) + \alpha\sigma_L(1) + \beta\sigma_T(1) \quad \text{Formula 2}$$

$$s(2) = s_e(2) + \alpha\sigma_L(2) + \beta\sigma_T(2) \quad \text{Formula 3}$$

In each of the first sample and the second sample, as shown in FIG. 4, a load is applied to the back surface 11b of the diaphragm 11, and the amount of phase change relative to the load is actually measured and calculated by dividing the amount of phase change by the load. That is, s(1) and s(2) are actually measured. Furthermore, $s_e(1)$, $s_e(2)$, $\sigma_L(1)$, $\sigma_L(2)$, $\sigma_T(1)$, and $\sigma_T(2)$ are calculated with the finite element method (FEM). The simultaneous equations of Formula 2 and Formula 3 are solved using the above values so as to obtain α and β. As shown in Table 1, in the first comparative example, the first acoustoelastic coefficient α of the SAW material having the ScAlN/SiC structure has a negative value, and the absolute value is relatively large. For this reason, the acoustoelasticity lowers the detection sensitivity of the SAW sensor of the first comparative example.

In contrast, according to the present embodiment in which the SAW material has the ScAlN/sapphire structure, both of the first acoustoelastic coefficient α and the second acoustoelastic coefficient β are relatively very small, compared with the first comparative example. Therefore, the detection sensitivity of the SAW sensor of the present embodiment can be raised since the influence of the acoustoelastic effect is very small.

Figure 7:
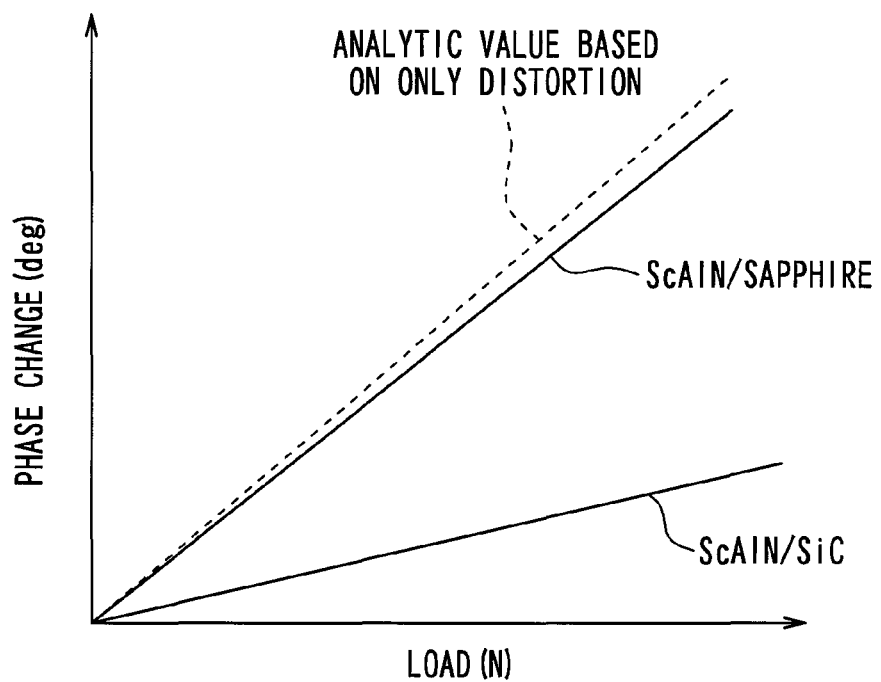
FIG. 7 is a graph illustrating a relationship between a load and a phase change in case where a SAW material having ScAlN/sapphire structure is used and in case where a SAW material having ScAlN/SiC structure is used.

FIG. 7 illustrates a relationship between the load (N) and the amount of phase change (deg) in each of the SAW sensor of this embodiment using the SAW material having the ScAlN/sapphire structure and the SAW sensor of the first comparative example using the SAW material having the ScAlN/SiC structure. FIG. 7 is obtained by experiments. The analytic value based on only distortion in FIG. 7 is result of analyzing the amount of phase change relative to the load by assuming that α=0 and β=0 in Formula 1. Moreover, the conditions of the sensor chips of this embodiment and the first comparative example are the same as the experiments conducted for obtaining α and β. Moreover, the thickness of the respective sensor chip is adjusted so that $s_e$ becomes the same between the sensor chips.

As shown in FIG. 7, in the SAW sensor of this embodiment having the ScAlN/sapphire structure, the amount of phase change is close to the analytic value, while the amount of phase change is about ⅓ of the analytic value in the SAW sensor of the first comparative example with the ScAlN/SiC structure. Therefore, also from the experimental result shown in FIG. 7, the detection sensitivity of SAW sensor of present embodiment is higher than the SAW sensor of the first comparative example because the influence of acoustoelastic effect is very small in the present embodiment.

In this embodiment, Sezawa wave is used as SAW. However, Rayleigh wave may be used as SAW. While the similar effect is acquired as this embodiment when Rayleigh wave is used, it may be desirable to use Sezawa wave for the following reason.

It is known that the distribution ratio of the SAW energy into the substrate becomes larger in the depth direction as the mode of SAW is made higher-order, in a SAW material having a general structure, in which a piezoelectric thin film is arranged on a substrate. In other words, as the mode of SAW is made higher-order, the SAW energy can be distributed to the deep side deeper from the surface of SAW material. For this reason, compared with a case where Rayleigh wave is used, the sapphire board strongly affects the acoustoelastic effect when using Sezawa wave, such that the acoustoelastic effect can be reduced. Therefore, when Sezawa wave is used, the detection sensitivity can be much improved.

Second Embodiment

The SAW sensor of this embodiment detects physical quantity such as tensile stress, compression stress or distortion.

Figure 8:
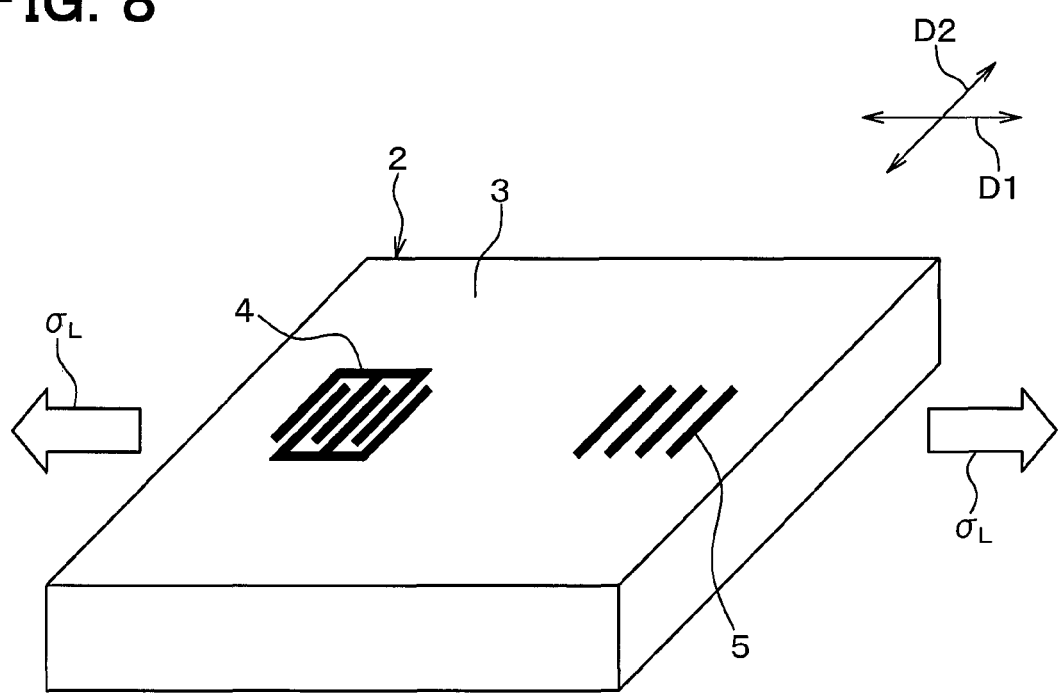
FIG. 8 is a perspective view illustrating a sensor chip of SAW sensor according to a second embodiment.
Figure 9:
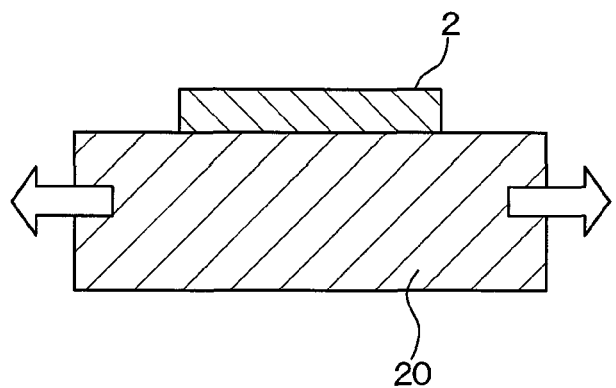
FIG. 9 is a sectional view illustrating the sensor chip of the second embodiment arranged on an object.

As shown in FIG. 9, the sensor chip 2 is disposed on an object 20 to which stress or distortion to be detected is applied. As shown in FIG. 8, the sensor chip 2 has similar configuration as that of the first embodiment. The sensor chip 2 is installed so that the tensile stress direction and the propagation direction D1 of SAW are in agreement when tensile stress is impressed to the object 20 in an axial direction as shown in an arrow in FIG. 9. This is the same when compression stress or distortion is impressed to the object 20 in an axial direction.

When stress is impressed to the object 20 in the axial direction, as show in FIG. 8, tensile stress $\sigma_L$ is applied to the sensor chip 2 in the propagation direction of SAW. At this time, since the phase of reflective wave changes, stress and distortion can be detected based on the amount of phase change that is related to stress and distortion.

The detection sensitivity of SAW sensor is expressed with the following Formula 4 in this embodiment.

$$s=s_e+\alpha\sigma_L \qquad \text{Formula 4}$$

Also in this embodiment, the detection sensitivity is improved since the acoustoelastic effect affecting the detection sensitivity is small, compared with a case where the SAW material having the ScAlN/SiC structure is used.

Third Embodiment

The SAW sensor of this embodiment detects acceleration as physical quantity.

Figure 10:
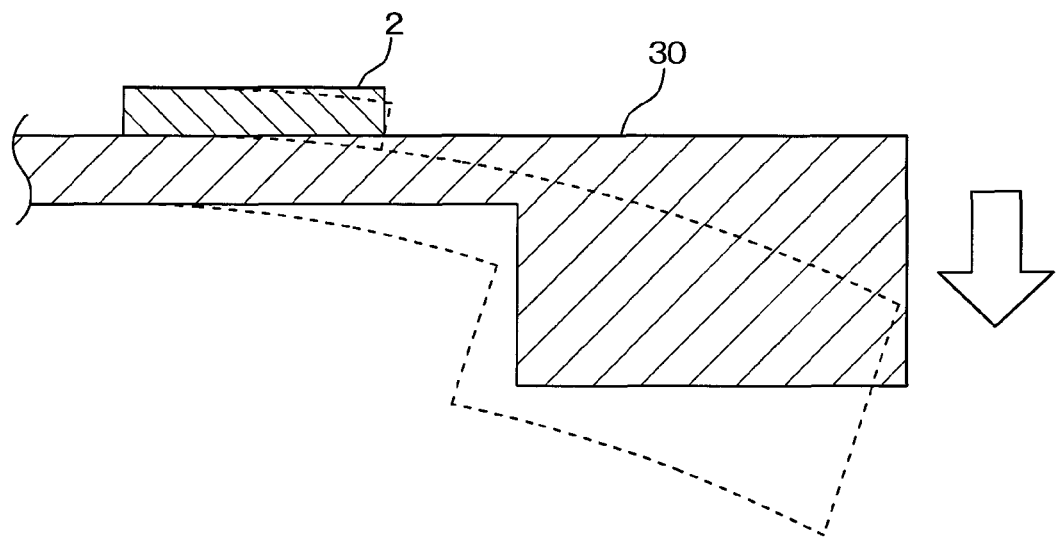
FIG. 10 is a sectional view illustrating a sensor chip of SAW sensor according to a third embodiment arranged on a deforming object.

As shown in FIG. 10, the sensor chip 2 is installed on the deforming object 30 which is distorted and deformed in one axial direction when acceleration is impressed. The sensor chip 2 has the similar configuration as that of the first embodiment. The sensor chip 2 is installed so that the distortion direction of the deforming object 30 and the propagation direction D1 of SAW are in agreement. When acceleration is impressed to the deforming object 30, tensile stress $\sigma_L$ is applied to the sensor chip 2 in the propagation direction of SAW, similarly to the second embodiment. At this time, since the phase of reflective wave changes, the acceleration is detected based on the amount of phase change that is related to acceleration.

Also in this embodiment, the detection sensitivity is improved similarly to the second embodiment.

Fourth Embodiment

In the second and third embodiments, the sensor chip 2 is installed at the position where only tensile stress $\sigma_L$ in the propagation direction of SAW is applied to the sensor chip 2 due to physical quantity such as stress.

Figure 11:
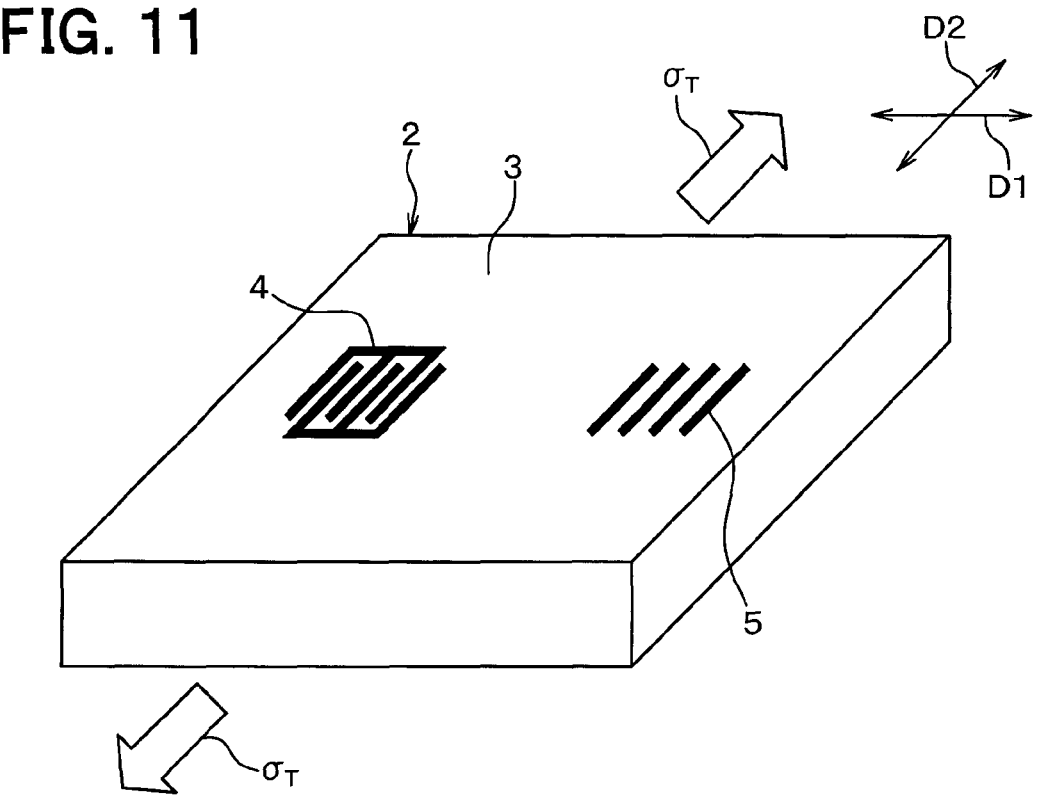
FIG. 11 is a perspective view illustrating a sensor chip of SAW sensor according to a fourth embodiment.

In the fourth embodiment, as shown in FIG. 11, the sensor chip 2 is installed at a position where only tensile stress $\sigma_T$ in the perpendicular direction perpendicular to the propagation direction of SAW is applied to the sensor chip 2 due to physical quantity such as stress.

The detection sensitivity of SAW sensor is expressed with the following Formula 5 in this embodiment.

$$s=s_e+\beta\sigma_T \qquad \text{Formula 5}$$

As explained in the first embodiment, since the SAW material 3 having the ScAlN/sapphire structure has very small second acoustoelastic coefficient $\beta$, the detection sensitivity of the SAW sensor of this embodiment becomes high.

Fifth Embodiment

Figure 12:
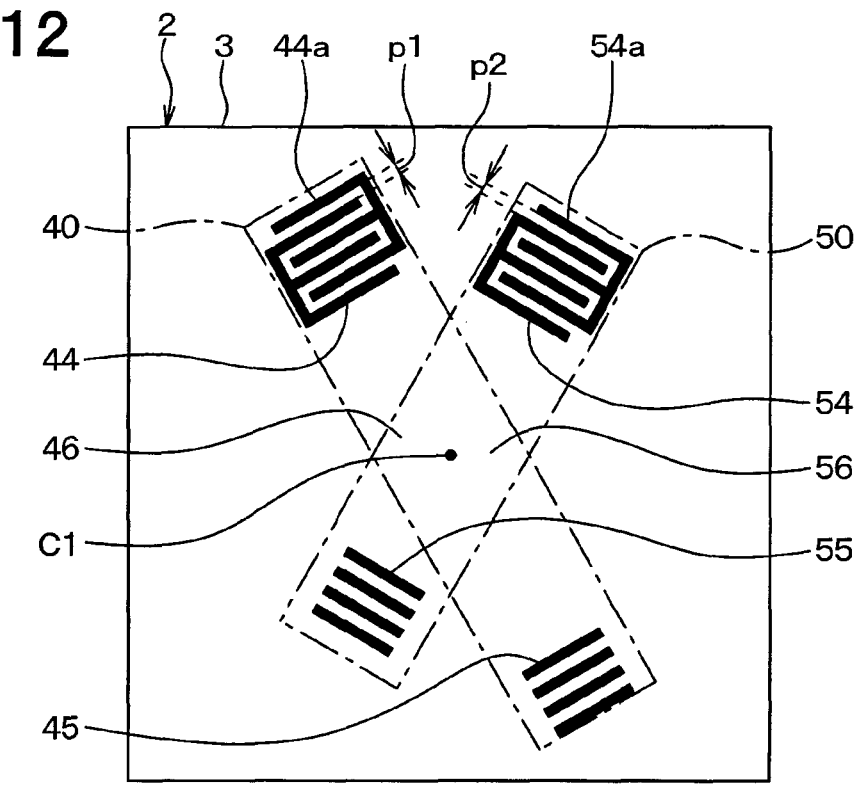
FIG. 12 is a plan view illustrating a sensor chip of SAW sensor according to a fifth embodiment.

As shown in FIG. 12, the sensor chip 2 of this embodiment has the Sezawa wave comb-teeth electrode 44 for Sezawa wave and the Rayleigh wave comb-teeth electrode 54 for Rayleigh wave on the surface of the SAW material 3.

The SAW material 3 has the similar configuration as that of the first embodiment. The Sezawa wave comb-teeth electrode 44 and the Rayleigh wave comb-teeth electrode 54 correspond to the comb-teeth electrode 4 of the first embodiment. The Sezawa wave comb-teeth electrode 44 is configured to excite Sezawa wave. The Rayleigh wave comb-teeth electrode 54 is configured to excite Rayleigh wave.

Specifically, the comb-teeth parts 44a of the Sezawa wave comb-teeth electrode 44 have a pitch p1 as a clearance therebetween, and the comb-teeth parts 54a of the Rayleigh wave comb-teeth electrode 54 have a pitch p2 as a clearance therebetween. The pitch p1 and the pitch p2 are different from each other. The pitch p1 and the pitch p2 are set in a manner that frequency of a drive signal for driving the comb-teeth electrode 44 and frequency of a drive signal for driving the comb-teeth electrode 54 become the same. The pitch p1 is an interval of the comb-teeth parts 44a adjacent to each other in the Sezawa wave comb-teeth electrode 44. Similarly, the pitch p2 is an interval of the adjacent comb-teeth parts 54a in the Rayleigh wave comb-teeth electrode 54. The drive signal is a high frequency signal impressed to the comb-teeth electrodes 44 and 54 to excite SAW to the SAW material 3 by driving the comb-teeth electrodes 44 and 54.

For example, when a radio drive system is adopted for the comb-teeth electrodes 44 and 54, a coil is electrically connected to each of the comb-teeth electrodes 44 and 54. While there is a frequency characteristic in a coil, the coil connected to the comb-teeth electrode 44 and the coil connected to the comb-teeth electrode 54 can be made common by making the frequency of the drive signal the same between the comb-teeth electrodes 44 and 54.

The pitch p1 of the Sezawa wave comb-teeth electrode 44 and the pitch p2 of the Rayleigh wave comb-teeth electrode 54 may be made the same. In this case, coils having different frequency characteristics are electrically connected to the comb-teeth electrodes 44 and 54, respectively.

The reflector 45 is formed on the surface of the SAW material 3 to correspond to the Sezawa wave comb-teeth electrode 44 as a Sezawa wave correspondence electrode. The reflector 45 reflects Sezawa wave excited by the Sezawa wave comb-teeth electrode 44. The domain between the comb-teeth electrode 44 and the reflector 45 on the surface of the SAW material 3 defines the Sezawa wave propagation path 46 in which Sezawa wave spreads. The reflective delay type Sezawa wave element 40 is configured by the comb-teeth electrode 44, the reflector 45, and the propagation path 46 for Sezawa waves.

Similarly, the reflector 55 is formed on the surface of the SAW material 3 to correspond to the Rayleigh wave comb-teeth electrode 54 as a Rayleigh wave correspondence electrode. The reflector 55 reflects Rayleigh wave excited by the Rayleigh wave comb-teeth electrode 54. The domain between the comb-teeth electrode 54 and the reflector 55 on the surface of the SAW material 3 defines the Rayleigh wave propagation path 56 in which Rayleigh wave spreads. The reflective delay type Rayleigh wave element 50 is configured by the comb-teeth electrode 54, the reflector 55, and the propagation path 56 for Rayleigh waves.

Thus, in this embodiment, two elements having different modes in Rayleigh wave type surface acoustic wave, e.g., the Sezawa wave element 40 and the Rayleigh wave element 50, are formed in the one sensor chip 2.

The Sezawa wave element 40 and the Rayleigh wave element 50 are arranged so that the center of gravity in the element domain is positioned at the center C1 of the sensor chip 2. A part of the Sezawa wave propagation path 46 and a part of the Rayleigh wave propagation path 56 overlap with each other. For this reason, the temperature in the element domain becomes almost the same between the Sezawa wave element 40 and the Rayleigh wave element 50.

When a part of the propagation path 46 and a part of the propagation path 56 overlap with each other, the center of gravity in the element domain may not be located at the center C1 of the sensor chip 2. In this case, the average temperature in the whole of the element domain can be made close between the Sezawa wave element 40 and the Rayleigh wave element 50 by making a part of the propagation path 46 and a part of the propagation path 56 overlap with each other.

Similarly to the first embodiment, the Sezawa wave element 40 is used for detecting physical quantity such as pressure, and corresponds to a first element that detects physical quantity. The Rayleigh wave element 50 is used as a temperature compensating element for correcting the amount of phase change based on a temperature change, and corresponds to a second element for temperature compensating.

When the sensor chip 2, i.e., SAW material 3, is distorted by physical quantity, the phase of SAW reflected with the reflector 45 and received with the comb-teeth electrode 44 change relative to the phase of SAW excited with the comb-teeth electrode 44 of the Sezawa wave element 40. The change amount in the phase is detected as a sensor output, and physical quantity such as pressure is detected based on the detected change amount in the phase.

At this time, since the influence of the acoustoelastic effect is small, the sensor output of the Sezawa wave element 40 is large relative to a distortion change of the SAW material 3. In contrast, the sensor output of the Rayleigh wave element 50 is small relative to a distortion change of the SAW material 3, since the influence of the acoustoelastic effect is large, compared with the Sezawa wave element 40. That is, the detection sensitivity relative to a distortion change is smaller in the Rayleigh wave element 50, compared with the Sezawa wave element 40.

The change in the phase of the reflective delay type SAW element is produced by a temperature change. Generally, the temperature characteristics (that is sensitivity to a temperature change) differs between the Sezawa wave element 40 and the Rayleigh wave element 50.

For this reason, similarly to the first embodiment, when the sensor chip 2 is installed on the diaphragm 11 to detect physical quantity such as pressure, the distortion of the sensor chip 2 and the temperature of the sensor chip 2 change by change in pressure and temperature of an object to be measured. In this case, the sensor output corresponds to the sum of the sensor output by the distortion change and the sensor output by the temperature change.

The correction based on the temperature becomes possible by combining the sensor output of the Sezawa wave element 40 and the sensor output of the Rayleigh wave element 50. Specifically, each temperature characteristics of the Sezawa wave element 40 and the Rayleigh wave element 50 is obtained in advance. The simultaneous equations as to each sensor output can be solved based on the temperature characteristics and the sensor output of the Sezawa wave element 40 and the Rayleigh wave element 50. Thus, the sensor output by the temperature change can be canceled from the sensor output of the Sezawa wave element 40.

According to the present embodiment, the Sezawa wave element 40 and the Rayleigh wave element 50 are formed in the one sensor chip 2, i.e., on the same SAW material 3. The Sezawa wave element 40 is used as an element for detecting physical quantity, and the Rayleigh wave element 50 is used as an element for temperature compensating.

As a second comparison example, a SAW element having the same mode as the SAW element for detecting physical quantity is used as a SAW element for temperature compensating. In the second comparison example, when the SAW element for temperature compensating is distorted by physical quantity, it is not possible to cancel only the sensor output by a temperature change even by combining the both sensor outputs of the SAW elements.

For this reason, the SAW element for temperature compensating needs to be arranged at a position where the SAW element for temperature compensating does not receive distortion and has a temperature similar or close to a temperature of the SAW element for detecting physical quantity.

However, it is generally difficult to find such a position in a small sensor chip. Since the reflective delay type SAW element has a large element domain, it is more difficult to select such a place in one sensor chip.

According to the embodiment, the detection sensitivity relative to a distortion change differs between the Sezawa wave element 40 and the Rayleigh wave element 50, and a difference in the detection sensitivity relative to a temperature change is known in advance. For this reason, if the Rayleigh wave element 50 is arranged at the place easy to receive distortion, the temperature compensating is possible by combining both of the sensor outputs, since the sensor output relative to a distortion change differs between the Sezawa wave element 40 and the Rayleigh wave element 50.

Therefore, it is not necessary to arrange the temperature compensating element, in this embodiment, at the place distant from the physical quantity detecting element which is distorted by physical quantity. For this reason, the Rayleigh wave element 50 for temperature compensating can be arranged near the Sezawa wave element 40 for detecting physical quantity within the one sensor chip 2. Further, the elements 40 and 50 are arranged such that the propagation paths 46 and 56 of the elements 40 and 50 are overlapped with each other. Thereby, the Rayleigh wave element 50 for temperature compensating can be made to have the same temperature as the Sezawa wave element 40 for physical quantity detection. Thus, this embodiment uses acoustoelastic phenomenon and its mode dependency.

The temperature compensating is explained more concretely. Similarly to the second comparison example, when a SAW element having the same mode as the SAW element for physical quantity detection is used as a SAW element for temperature compensating, the temperature compensating SAW element is installed at a place distant from the SAW element for physical quantity detection within the same sensor chip. At this time, the temperature compensating can be made by solving the following simultaneous equations (Formula 6 and Formula 7).

$$s1 = \alpha\epsilon1 + \beta T1 \quad \text{Formula 6}$$

$$s2 = \alpha\epsilon2 + \beta T2 \quad \text{Formula 7}$$

s1: signal output of the SAW element for physical quantity detection $\epsilon1$: distortion at a portion where the SAW element for physical quantity detection is installed T1: temperature of a portion where the SAW element for physical quantity detection is installed s2: signal output of the SAW element for temperature compensating $\epsilon2$: distortion at a portion where the SAW element for temperature compensating is installed T2: temperature of a portion where the SAW element for temperature compensating is installed $\alpha$: output sensitivity relative to distortion of both the elements $\beta$: output sensitivity relative to temperature of both the elements $\alpha$ and $\beta$ are beforehand obtained by experiments.

In this case, since there are four unknowns ($\epsilon1$, $\epsilon2$, T1, T2), it is most desirable to find the setting position of the SAW element for temperature compensating with T1=T2 and $\epsilon2$=0 in order to solve the simultaneous equations, but it is almost impossible.

In order to solve the simultaneous equations, it is necessary to know the relationship between T1 and T2 (for example, the difference is always regular) and to know the relationship between $\epsilon1$ and $\epsilon2$ (for example, by calculating the ratio by FEM). However, it is common that the difference between T1 and T2 becomes larger as the temperature becomes higher, and an error is caused by this when solving the simultaneous equations.

In contrast, the simultaneous equations in this embodiment are shown by the following Formula 8 and Formula 9.

$$s1 = \alpha1\epsilon1 + \beta1 T1 \quad \text{Formula 8}$$

$$s2 = \alpha2\epsilon2 + \beta2 T2 \quad \text{Formula 9}$$

s1, $\epsilon1$, T1, s2, $\epsilon2$, and T2 are the same as Formula 6 and Formula 7.

$\alpha1$ is output sensitivity relative to the distortion of the SAW element for physical quantity detection, and $\beta1$ is output sensitivity relative to the temperature of the SAW element for physical quantity detection. $\alpha1$ and $\beta1$ are beforehand calculated by experiments.

$\alpha2$ is output sensitivity relative to the distortion of the SAW element for temperature compensating, and $\beta2$ is output sensitivity relative to the temperature of the SAW element for temperature compensating. $\alpha2$ and $\beta2$ are beforehand calculated by experiments.

The SAW element for physical quantity detection corresponds to a Sezawa wave element 40, and the SAW element for temperature compensating corresponds to the Rayleigh wave element 50.

In this case, $\alpha1$, $\alpha2$, $\beta1$, and $\beta2$ are known in advance. According to this embodiment, the elements 40 and 50 are arranged to make the propagation paths 46 and 56 to overlap with each other, thereby assuming that $\epsilon1=\epsilon2$ and T1=T2 with remarkable accuracy. Therefore, according to this embodiment, the simultaneous equations (Formula 8 and Formula 9) can be solved with sufficient accuracy.

While a part of the Sezawa wave propagation path 46 and a part of the Rayleigh wave propagation path 56 overlap with each other in this embodiment, the propagation path 46 and the propagation path 56 may not overlap with each other. The Sezawa wave element 40 and the Rayleigh wave element 50 are arranged so that the temperature and distortion in the element domains are close to each other.

Other Embodiment

The present disclosure is not limited to the above embodiments, and can be suitably modified within the scope of the present disclosure as defined by the appended claims.

The ScAlN film 8 is not limited to be directly formed on the surface of the sapphire board 7. The ScAlN film 8 may be formed on the surface of the sapphire board 7 through $SiO_2$ film.

The electrodes (such as the comb-teeth electrode 4) are not limited to be formed on the upper surface 8a of the ScAlN film 8. The electrodes may be formed on the lower surface of the ScAlN film 8, in other words, the electrodes may be formed between the ScAlN film 8 and the sapphire board 7.

The electrode structure of the SAW element is not limited to the reflective delay type. The electrode structure of the SAW element may be a transversal filter type or a resonated type.

In the case of transversal type, a driving comb-teeth electrode for exciting SAW and a receiving comb-teeth electrode for receiving SAW are formed in the SAW material as the electrodes. In this case, the receiving comb-teeth electrode corresponds to a correspondence electrode prepared to correspond to the driving comb-teeth electrode.

In the case of resonated type, at least the driving comb-teeth electrode is made on the SAW material as the electrode. In this case, in Formula 1 explained in the first embodiment, "s" represents a value calculated by dividing a change amount in resonance frequency by a load, and "$s_e$" represents a value calculated by dividing a change amount in resonance frequency caused by an extension in the length of the propagation path by a load.

The above-mentioned embodiments may be suitably combined with each other except for a case of being clearly improper. For example, the fifth embodiment may be combined not only with the first embodiment but with the second to the fourth embodiments.

The elements described in the above embodiment are not necessarily indispensable except for a case where it is clearly shown that the element is especially indispensable and a case where it is theoretically thought that the element is clearly indispensable.

Such changes and modifications are to be understood as being within the scope of the present disclosure as defined by the appended claims.

What is claimed is:

1. A surface acoustic wave sensor comprising:
a surface acoustic wave material to be arranged at a place where the surface acoustic wave material is distorted by physical quantity; and
a comb-teeth electrode arranged on the surface acoustic wave material to excite a surface acoustic wave to the surface acoustic wave material, wherein
the surface acoustic wave material has a sapphire board and a ScAlN film arranged on a surface of the sapphire board, and
the surface acoustic wave material is arranged at the place where a stress in a propagation direction of the surface acoustic wave and a stress in a perpendicular direction perpendicular to the propagation direction are applied to the surface acoustic wave material.

2. The surface acoustic wave sensor according to claim 1, wherein
a Sezawa wave is used as the surface acoustic wave.

3. The surface acoustic wave sensor according to claim 1, wherein
the comb-teeth electrode has
a Sezawa wave comb-teeth electrode that excites a Sezawa wave, and
a Rayleigh wave comb-teeth electrode that excites a Rayleigh wave,
the Sezawa wave comb-teeth electrode corresponds to a first element that detects physical quantity, and
the Rayleigh wave comb-teeth electrode corresponds to a second element for temperature compensating.

4. The surface acoustic wave sensor according to claim 3, wherein
the Sezawa wave comb-teeth electrode has a plurality of comb-teeth parts with a first pitch,
the Rayleigh wave comb-teeth electrode has a plurality of comb-teeth parts with a second pitch, and
the first pitch and the second pitch are different from each other, and are set such that a frequency of a drive signal for driving the Sezawa wave comb-teeth electrode and a frequency of a drive signal for driving the Rayleigh wave comb-teeth electrode are the same.

5. The surface acoustic wave sensor according to claim 3, further comprising:
a Sezawa wave correspondence electrode disposed on the surface acoustic wave material to correspond to the Sezawa wave comb-teeth electrode, the Sezawa wave correspondence electrode receiving or reflecting a Sezawa wave excited by the Sezawa wave comb-teeth electrode;
a Sezawa wave propagation path where a Sezawa wave spreads between the Sezawa wave comb-teeth electrode and the Sezawa wave correspondence electrode on the surface acoustic wave material;
a Rayleigh wave correspondence electrode disposed on the surface acoustic wave material to correspond to the Rayleigh wave comb-teeth electrode, the Rayleigh wave correspondence electrode receiving or reflecting a Rayleigh wave excited by the Rayleigh wave comb-teeth electrode; and
a Rayleigh wave propagation path where a Rayleigh wave spreads between the Rayleigh wave comb-teeth electrode and the Rayleigh wave correspondence electrode on the surface acoustic wave material, wherein
a part of the Sezawa wave propagation path and a part of the Rayleigh wave propagation path overlap with each other.

6. The surface acoustic wave sensor according to claim 1, wherein
a substrate surface of the sapphire board has a plane direction of C-plane, and
the propagation direction is inside of A-plane or in a direction defined by rotating by 60 degrees relative to the A plane.

7. A surface acoustic wave sensor comprising:
a surface acoustic wave material to be arranged at a place where the surface acoustic wave material is distorted by a physical quantity; and
a comb-teeth electrode arranged on the surface acoustic wave material to excite a surface acoustic wave to the surface acoustic wave material, wherein
the surface acoustic wave material has a sapphire board and a ScAlN film arranged on a surface of the sapphire board,
the comb-teeth electrode has
a Sezawa wave comb-teeth electrode that excites a Sezawa wave, and
a Rayleigh wave comb-teeth electrode that excites a Rayleigh wave,
the Sezawa wave comb-teeth electrode corresponds to a first element that detects physical quantity, and
the Rayleigh wave comb-teeth electrode corresponds to a second element for temperature compensating.

8. The surface acoustic wave sensor according to claim 7, wherein
the Sezawa wave comb-teeth electrode has a plurality of comb-teeth parts with a first pitch,
the Rayleigh wave comb-teeth electrode has a plurality of comb-teeth parts with a second pitch, and
the first pitch and the second pitch are different from each other and are set such that a frequency of a drive signal for driving the Sezawa wave comb-teeth electrode and a frequency of a drive signal for driving the Rayleigh wave comb-teeth electrode are the same.

9. The surface acoustic wave sensor according to claim 7, further comprising:
a Sezawa wave correspondence electrode disposed on the surface acoustic wave material to correspond to the Sezawa wave comb-teeth electrode, the Sezawa wave correspondence electrode receiving or reflecting a Sezawa wave excited by the Sezawa wave comb-teeth electrode;
a Sezawa wave propagation path where a Sezawa wave spreads between the Sezawa wave comb-teeth electrode and the Sezawa wave correspondence electrode on the surface acoustic wave material;
a Rayleigh wave correspondence electrode disposed on the surface acoustic wave material to correspond to the Rayleigh wave comb-teeth electrode, the Rayleigh wave correspondence electrode receiving or reflecting a Rayleigh wave excited by the Rayleigh wave comb-teeth electrode; and
a Rayleigh wave propagation path where a Rayleigh wave spreads between the Rayleigh wave comb-teeth electrode and the Rayleigh wave correspondence electrode on the surface acoustic wave material, wherein
a part of the Sezawa wave propagation path and a part of the Rayleigh wave propagation path overlap with each other.

10. The surface acoustic wave sensor according to claim 7, wherein
- a substrate surface of the sapphire board has a plane direction of C-plane, and
- the propagation direction is inside of A-plane or in a direction defined by rotating by 60 degrees relative to the A-plane.

11. The surface acoustic wave sensor according to claim 7, wherein the surface acoustic wave material is arranged at the place where a stress in a propagation direction of the surface acoustic wave and a stress in a perpendicular direction perpendicular to the propagation direction are applied to the surface acoustic wave material.

* * * * *